(12) United States Patent
Townsend et al.

(10) Patent No.: US 6,599,268 B1
(45) Date of Patent: Jul. 29, 2003

(54) HYPODERMIC SYRINGE WITH A SELECTIVELY RETRACTABLE NEEDLE

(75) Inventors: Scott A. Townsend, Holdrege, NE (US); Roger Hoeck, Holdrege, NE (US); Charles L. Bush, Jr., Fairfield, NJ (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 239 days.

(21) Appl. No.: 09/604,429

(22) Filed: Jun. 27, 2000

(51) Int. Cl.[7] .............................................. A61M 5/00
(52) U.S. Cl. ...................................... 604/110; 604/195
(58) Field of Search ................................ 604/110, 187, 604/193, 194, 198, 220, 195, 197, 218, 239, 240; 128/919

(56) References Cited

U.S. PATENT DOCUMENTS

| | | | |
|---|---|---|---|
| 4,534,827 A | * 8/1985 | Henderson | 216/101 |
| 4,838,869 A | 6/1989 | Allard | 604/195 |
| 4,900,307 A | 2/1990 | Kulli | 604/110 |
| 4,994,034 A | 2/1991 | Botich et al. | 604/110 |
| 5,019,044 A | 5/1991 | Tsao | 604/110 |
| 5,049,133 A | 9/1991 | Villen Pascual | 604/110 |
| 5,053,010 A | 10/1991 | McGary et al. | 604/110 |
| 5,180,369 A | 1/1993 | Dysarz | 604/110 |
| 5,180,370 A | 1/1993 | Giillespie | 604/110 |
| 5,188,599 A | 2/1993 | Botich et al. | 604/110 |
| 5,201,710 A | 4/1993 | Caselli | 604/110 |
| 5,385,551 A | 1/1995 | Shaw | 604/110 |
| 5,407,436 A | 4/1995 | Toft et al. | 604/195 |
| 5,752,059 A | 5/1998 | Holleran | 395/800 |
| 5,769,822 A | 6/1998 | McGary et al. | 604/110 |
| 5,826,062 A | 10/1998 | Fake, Jr. | 395/500 |
| 5,917,489 A | 6/1999 | Thurlow | 345/347 |
| 6,010,486 A | 1/2000 | Carter et al. | 604/195 |
| 6,036,674 A | 3/2000 | Caizza et al. | |
| 6,088,696 A | 7/2000 | Moon | 707/10 |
| 6,183,440 B1 | * 2/2001 | Bell | 604/110 |
| 6,189,026 B1 | 2/2001 | Birrell | 709/206 |
| 6,205,432 B1 | 3/2001 | Gabbard | 705/14 |
| 6,249,807 B1 | 6/2001 | Shaw | 709/206 |
| 6,368,303 B1 | * 4/2002 | Caizza | 604/110 |

* cited by examiner

*Primary Examiner*—Brian L. Casler
*Assistant Examiner*—Mark K. Han
(74) *Attorney, Agent, or Firm*—Jeanne P. Lukasavage

(57) ABSTRACT

A syringe has a retractable needle and a barrel having an open proximal end and an open distal end defining a receiver with an inward shoulder. The barrel has a hollow bore, an elongate plunger with a proximal end and a distal open end with a cavity therewithin. A stopper occludes the open end of the cavity. The syringe has an elongate hub with a proximal flange. The hub is within and sized for slidable movement within the receiver at the distal end of the barrel with the flange defining a distal end of a chamber. There is a sleeve sized to fit with a clearance about the hub disposed between the shoulder and the flange when the hub is in the receiver, the sleeve having a sharpened proximal end disposed against the flange. The needle has a pointed distal end and a proximal end connected to the passageway of the hub with the pointed end of the needle extending outwardly. There is a spring disposed about the hub compressed to provide a bias between the receiver and the flange so that when a force greater than required to expel fluid from the chamber is applied, the plunger causes the cutting surface to cut through the flange and stopper and expose the cavity to allow the spring to urge the hub into the cavity in the plunger and retract the needle to a position within the syringe.

16 Claims, 9 Drawing Sheets

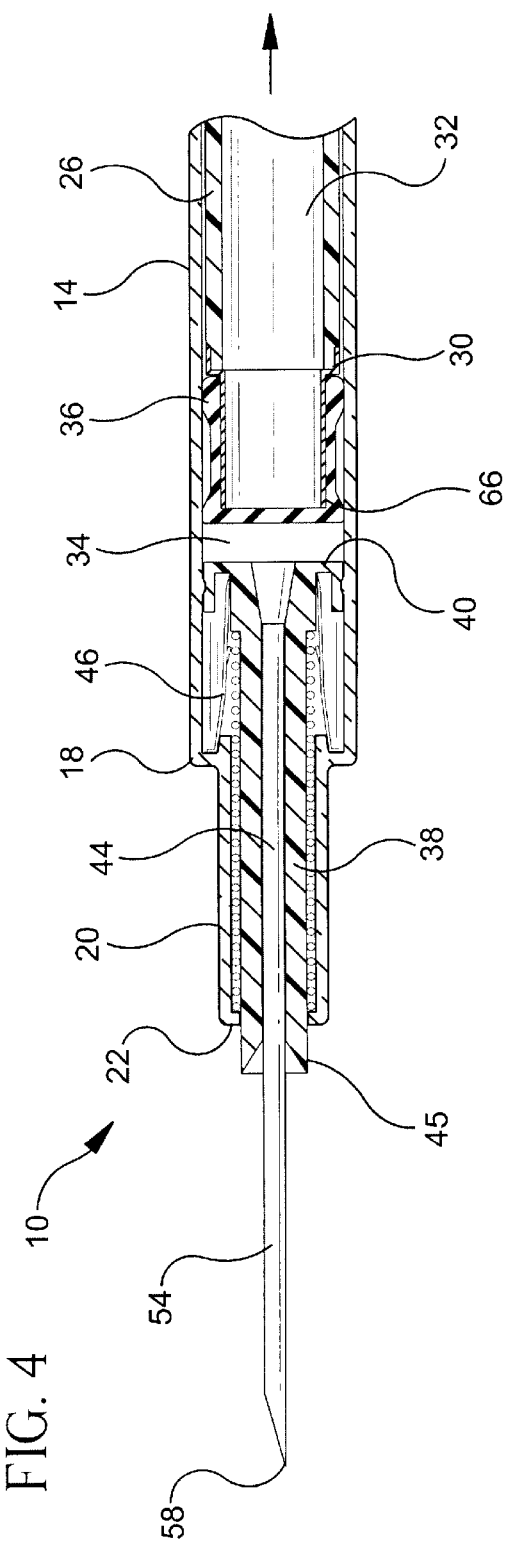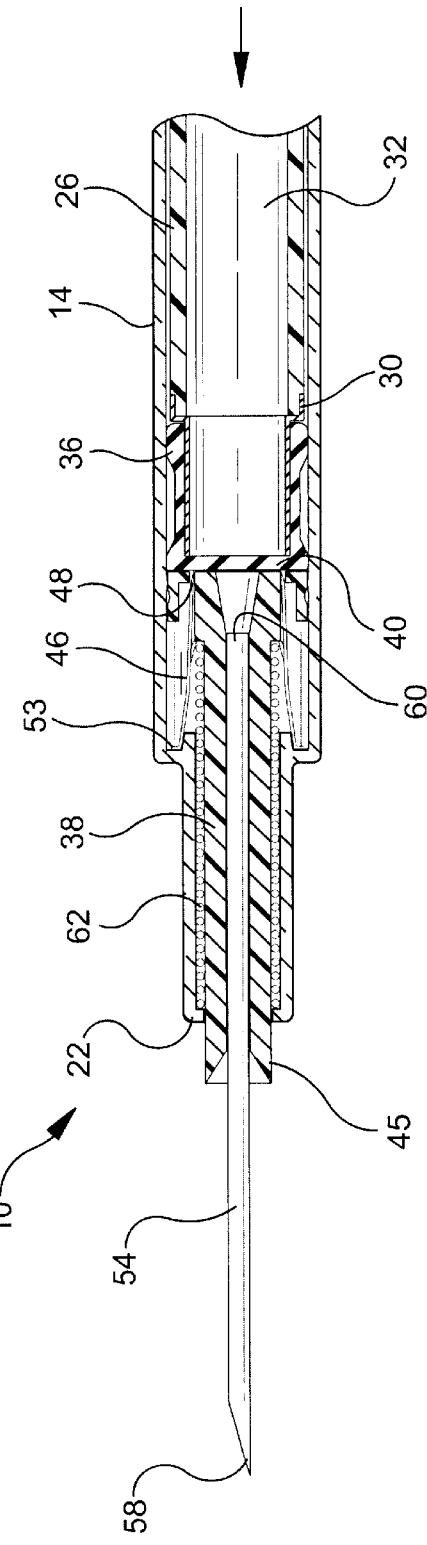
FIG. 4
FIG. 5

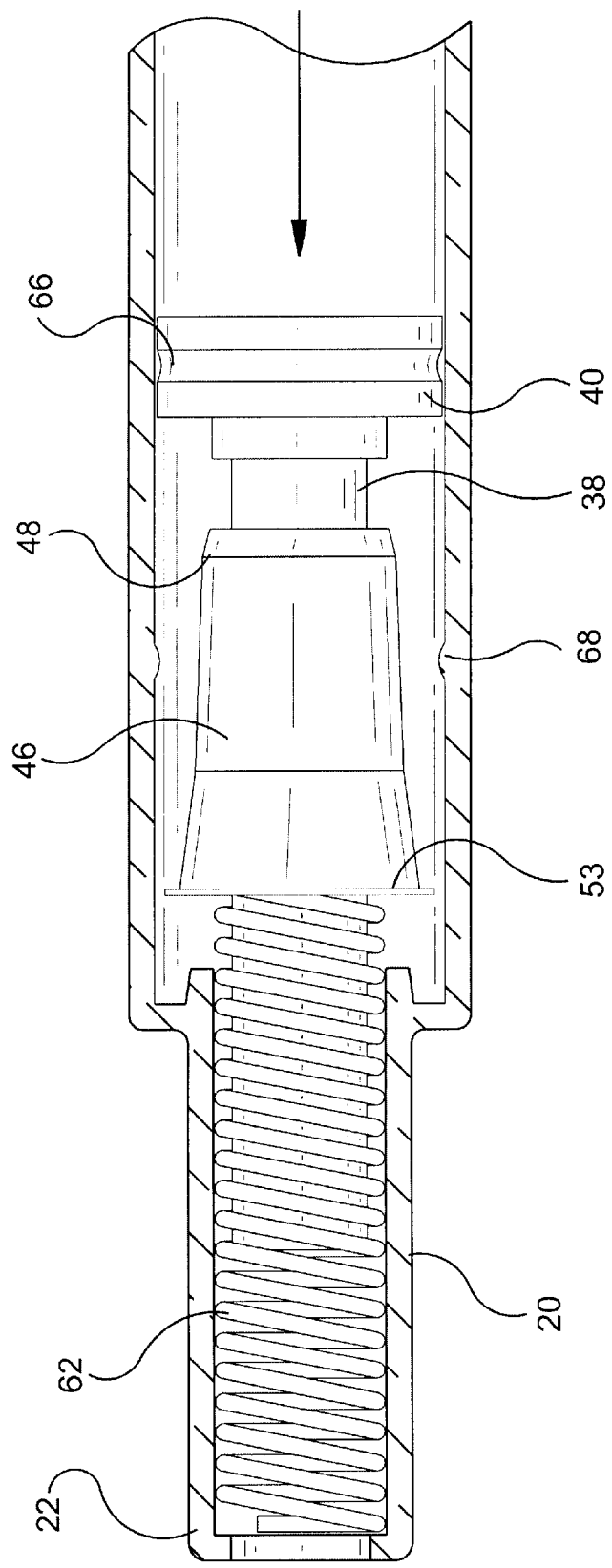

HYPODERMIC SYRINGE WITH A SELECTIVELY RETRACTABLE NEEDLE

FIELD OF INVENTION

The present invention is generally related to hypodermic syringes and more particularly to syringes that include a needle that is retractable after the intended use to substantially prevent inadvertent exposure to the needle and reuse of the syringe.

BACKGROUND

Hypodermic syringes are widely used in the medical arts for administering medicaments and for drawing body fluid samples. Generally, hypodermic syringes have a metal needle attached either fixedly or removably that has a sharpened distal point for penetrating vial stoppers or patient's skin. The hypodermic syringes and needles have been used for many years with few problems reported when the vast numbers and needles being used are considered. More recently, with the recognition of viral diseases that are transmitted by body fluids and greater sensitivity of the need to protect health care workers from inadvertent contact with previously used needles (commonly referred to as "sharps") as well as the need to reduce criminal misuse of improperly disposed of needles and syringes, syringes and needles that include provisions to prevent reuse have been developed.

Provisions intended to prevent reuse of needles and syringes include a variety of sharps collector systems that are widely used in health care facilities. Other developments include needle attachments that may be readily broken off by practitioners once the syringe has completed its intended use. A variety of shielding mechanisms have been developed, some of which are currently commercially available. While many of these developments have reduced the incidence of inadvertent exposure of healthcare workers to sharps, most of these devices can readily be overcome by an individual determined to obtain and misuse a hypodermic syringe and needle. As a result of this problem, further developments in the art of hypodermic syringes have resulted in syringes with needles that withdraw into the body of the syringe once their intended use is completed.

U.S. Pat. No. 4,838,869 discloses a retractable hypodermic needle configured for one time use wherein the needle is spring loaded and automatically irretrievably retracted into the hypodermic syringe when the syringe plunger is fully depressed, whereby protrusions on the end of the plunger engage tabs holding the spring loaded needle to release the needle for retraction. A potential problem with the design disclosed in this patent is that many times a practitioner may draw and expel a fluid several times during preparation for administration of a medicament, with this design, the practitioner could inadvertently discharge the mechanism. Further, the design would be very difficult to manufacture in large volumes.

U.S. Pat. No. 4,900,307 discloses a hypodermic needle with an enlarged hub that provides provisions for selectively withdrawing the needle into the hub once the syringe and needle have completed their intended usage. While this disclosed design does substantially eliminate the problem of premature discharge of the retraction mechanism, the enlarged hub has a considerably "dead volume" that would result in a significant undeliverable retention of the medicament. Additionally, although the needle is secured in the hub after discharge, the syringe itself is still fully functional after the hub with the needle inside is removed.

U.S. Pat. No. 4,994,034 discloses a hypodermic injection system with a retractable needle wherein the needle retracts within the interior cavity of a syringe plunger. The disclosed invention includes a cylindrical spring housing with resilient fingers which capture a coiled spring that biasly holds a needle holder against the retaining force of the resilient fingers. The plunger in this disclosure has a frangible end, which when engaging the resilient fingers under a predetermined amount of force, dissociate which remaining inwardly-tapered shoulders spread the resilient fingers, allowing the coiled spring to eject the needle and its holder into the interior cavity of the syringe plunger. A syringe manufactured using this disclosure would be complex and difficult to assemble. It is believed that no successful commercial product has been produced using this disclosure.

U.S. Pat. No. 5,019,044 discloses a safety hypodermic syringe with a hypodermic needle fixed connected to a holder plate and constantly supported by a spring for making axial movement. The holder plate is normally retained by a clamp at a ready position for injection. When the plunger of the syringe is pushed to the bottom of the barrel, the needle is released from the clamp and is pushed by the spring to drop and further follow a rubber plug to be squeezed into a chamber in the plunger. Again, no successful commercial product has resulted from this disclosure, which would be complex to manufacture and appears to have a considerable undeliverable dead volume.

Another example of a syringe with a retractable needle is disclosed in U.S. Pat. No. 5,053,010. The disclosed syringe retracts the needle into a hollow plunger additional pressure on the plunger after the contents of the syringe are expelled. The disclosed design incorporates a sliding elastomeric seal which displaces from its forward position to a retracted position, thereby allowing additional forward travel of the plunger to actuate the retraction mechanism. A problem reported with this design is that, because of the soft nature of the seal, the seal may be prematurely displaced during its use in an injection. Attempts to overcome this difficulty by increasing the stiffness of the sealing member could impair the seal integrity.

U.S. Pat. No. 5,180,369 discloses a self destructive syringe assembly having a needle cannula fixed to a slidable piston. The slidable piston and slidable piston flange are held within the barrel of the syringe assembly by a compressed spring, a guide tube and a shatter ring. The plunger of the syringe assembly is a hollow elongated tube with a thumb flat at one end, a sliding gasket, a plunger shatter plate and a hook rim at the other end. The patent reports that when medicament is injected, the elongated hollow plunger is further thrust into the shatter ring, the shatter ring shatters, further allowing the slidable piston and slidable piston flange to thrust into the plunger shatter plate to shatter. The shattering of the plunger shatter plate causes the slidable piston and needle cannula to be thrust into the hollow plunger by the spring and is thus prevented from re-entering the guide tube. Again, no successful commercial product has resulted from this disclosure.

U.S. Pat. No. 5,180,370 discloses a syringe which has an internal mechanism for retracting the needle into the syringe after the injection has been given. In one disclosed embodiment, the needle is manually retracted by pulling back on the plunger, and in another, the needle is propelled by a compressed spring into a hollow chamber within the plunger. A syringe produced with this disclosure would be complex to manufacture, and no successful commercial product has resulted from this disclosure.

U.S. Pat. No. 5,188,599 discloses a hypodermic injection system with a needle that retracts within an interior cavity of the syringe plunger. The needle when retracted is held within the plunger. The disclosed device includes a cylindrical spring housing that has resilient fingers which capture a spring under bias holding a needle holder against the retaining force of resilient fingers. The plunger has a frangible end which dissociates when the outwardly tapered shoulders spread the resilient fingers, allowing the coiled spring to eject the needle and its holder into the interior cavity of the syringe plunger. The patent also discloses a body fluid sampling device that includes a double-ended needle for communication with an evacuated blood collection tube. This patent also includes a review of several earlier disclosures related to retractable needles. Attempts have been made to produce commercial products based on the disclosures of this patent, but as yet there is no successful commercial product.

U.S. Pat. No. 5,201,710 discloses a syringe fitted with a clamping device for the needle and with a mechanism to enable the needle to be automatically retractable into the syringe body at the end of an injection. The disclosed device includes inner and outer cylinders, openings at the ends of the outer cylinder, a third opening at an end of the inner cylinder and a closure for the third opening. The disclosed device further includes a needle with a head, a seal, a first spring to push the needle against the closure and a clamping device loaded by a second spring to maintain outward to the syringe and to release the needle. There is a diaphragm in the closure that bends before breaking and a sharp element to break the diaphragm. There also is a closure to prevent the needle from being accessible and a stop to prevent the second cylinder from being moved outwardly after the syringe is used. As is apparent from the description, the device disclosed by this patent is complex and would be difficult to assemble. No successful commercial product has resulted from the disclosure in this patent.

U.S. Pat. No. 5,385,551 discloses a non-reusable medical device that has a needle which is retractable by depression a plunger slidably mounted in the device. The disclosed device includes a front-mounted retraction mechanism that has a needle holder connected to the needle. The needle holder is supported along the axis of the device by a frictionally engaged retainer ring member coupled to the needle holder along an axially aligned sliding interface. The needle holder and retainer are positioned in the front portion of a hollow body. The front of a movable member or plunger presses against the retainer member passing around the needle holder which cannot move forward, thereby separating the retainer from the needle holder. The separation occurs by gradually reducing the extent of the sliding interface area until the retainer member pops loose from the needle holder whereupon the needle holder and needle are retracted into a cavity in the plunger in response to a retraction force applied to the needle holder by a previously compressed spring. Again, the device disclosed in this patent is complex, difficult to manufacture and appears to have significant undeliverable dead volume. Attempts have been made to commercialize products from this disclosure with only limited success.

U.S. Pat. No. 5,407,436 discloses a hypodermic syringe that has a hollow needle that is automatically retractable after use. The disclosed syringe includes a one-piece body molding has a main chamber for a plunger, sample container or drug cartridge, a forward chamber to house a spring to bias a needle holder, and internal latching formations to retain the needle holder with the spring compressed in the forward chamber until automatic retraction when the latching formations are released by end of plunger movement.

The patent discloses that the sealing between the plunger and the body is accomplished by an over-sized plunger head that forces head and wall deformation. The disclosed spring has seals at both ends for the forward chamber. The patent teaches that the needle, its holder, spring and seals can be installed using a sliding guide. In using a syringe produced using this disclosure, the practitioner would need to exercise care when drawing and expelling a fluid during filling, because the retraction of the needle is activated by depressing the plunger sufficiently to engage cooperating latches. The engagement occurs at the bottom of the stroke to expel fluid from the syringe.

U.S. Pat. No. 5,769,822 discloses a non-reusable syringe with a hollow plunger that has a seal member thereon. The position of the plunger and the seal relative to the barrel permits the plunger, with sufficient strength, to carry applied pressure through the device during injection of a fluid and yet permit the seal disposed at one end of the plunger to have maximum sealing integrity between the plunger and a cylindrical barrel disposed around the exterior of the plunger to abate leakage of the liquid in a chamber within the barrel, as the plunger is manipulated from an expanded position to and expended position and thereafter to a third or collapsed position.

U.S. Pat. No. 6,010,486 discloses a retracting needle syringe that substantially prevents reuse of the syringe by destroying the plunger rod and the needle hub and additionally, retracts the needle into the plunger rod. The disclosed syringe includes provisions that upon fully depressing the plunger rod and applying distally directed axial force, a frangible portion of the inner hub is broken and the plunger tip dislodges to allow a spring to urge a cutter to open the chamber inside the plunger.

Most of the devices discussed in the above referenced disclosures are somewhat complex, and many require manufacture and assembly of parts with potentially difficult assembly or tight tolerance requirements. Many of the designs depend upon a careful application of forces by the practitioner to draw and expel fluids from the syringe that if the tolerances between the multiple components of the device are not carefully adhered to during manufacture and assembly may result in premature activation of the retraction function of the syringe. Current conventional syringes are considered by users to be virtually fault-free and reliable. They are used for a variety of different procedures involving both "one-shot" fill and inject procedures, as well as more complex mixing measuring and delivery functions. In order for a retractable syringe to displace these functional, utilitarian and reliable conventional syringes, the retractable syringe should not significantly interfere with the users current practices, it needs to be substantially reliable and their cost should not be prohibitive. Current conventional syringes are often manufactured at rates of several hundred per minute and their cost is generally not a significant factor in their usage. Additionally every year, hundreds of millions of small capacity (one milliliter) syringes are used outside of the normal controlled health care environment by diabetics and other self-injectors who must daily accurately inject small amounts, often only a few tenths of a milliliter. These small capacity syringes are physically quite small, with an overall length of less than five inches and an inside bore diameter of less than one-quarter inch. Reviewing the disclosures above, one skilled in the art of high volume manufacturing recognizes that assembling hundreds of millions of most of these relatively complex devices with their retraction elements contained in such a small space as a one-quarter inch diameter bore is a daunting task.

Additionally, many of the disclosed devices have substantial undeliverable "dead volumes" that substantially confound many diabetics need for accurate measuring, mixing of more than one type of insulin in the syringe and delivering small doses of insulin. The need thus exists for a selectively retractable syringe that is compatible with a small capacity syringe, that is capable of being manufactured at high volumes and is sufficiently non-complex to be reliable in use when produced at volumes of hundreds of millions per year. Such a device is disclosed herein below.

SUMMARY

A hypodermic syringe of the invention that has a selectively retractable needle includes an elongate barrel having an open proximal end and an open distal end defining a receiver with an inward shoulder. The barrel has a hollow bore therethrough extending from the proximal end to the distal end. The syringe includes an elongate plunger with a proximal end and a distal open end, there is a cavity within the plunger extending proximally from the open distal end. The plunger is disposed and sized to fit within the bore of the barrel for a slidable movement to define a chamber for receiving and expelling fluids. The plunger has a stopper disposed at the distal end to occlude the open end of the cavity. The stopper is sized and shaped to form a slidable substantially fluid tight seal with the bore of the barrel for forming the chamber. The syringe of the invention has an elongate hub having with a proximal flange. The hub is disposed and sized for slidable movement within the receiver at the distal end of the barrel with the flange defining a distal end of the chamber in the barrel, the hub has a passageway therethrough. There is a sleeve sized to fit with a clearance about the hub. The sleeve is disposed about the hub between the shoulder and the flange when the hub is positioned in the receiver: the sleeve having a sharpened proximal end disposed substantially against a distal surface of the flange. The sleeve has at least one inward projection located distally to the cutting surface. There is an elongate needle having a fluid path therethrough. The needle has a pointed distal end and a proximal end connected to the passageway of the hub so that when the hub is disposed in the receiver at the distal end of the barrel, the pointed end of the needle extends distally outwardly and the fluid path of the needle is in fluid communication with the chamber of the barrel. There is an elongate spring disposed about the hub so that when the hub is positioned in the receiver, the spring is sufficiently compressed to provide a bias between the receiver and the flange on the hub. When a force greater than a force required to expel fluid from the chamber is applied to the plunger the hub is moved distally in the receiver a sufficient distance to cause the cutting surface of the sleeve to engage, to cut through the flange and to engage the at least one inward projection on the sleeve against the hub to allow the cutting surface of the sleeve to cut through the stopper to expose the cavity in the plunger. The opening of the cavity allows the bias of the spring to urge a sufficient movement of the hub into the cavity in the plunger to retract the needle to a position within the syringe where inadvertent contact with the pointed distal end is substantially prevented.

The syringe of the invention has an undeliverable "deadspace" volume substantially similar to conventional syringes. The syringe of the invention is as suitable for use in drawing, measuring, mixing and delivering small volumes of medicaments as conventional syringes. Unlike many of the devices disclosed above, the syringe of the invention is substantially unlikely to be inadvertently retracted by a user following currently used practices and procedures. The syringe of the invention does not depend on a user having to exercise substantially more care than with a conventional syringe when drawing and mixing fluids in the syringe to avoid inadvertent activation, and importantly, the syringe of the invention is compatible with the efficiency of high volume automated manufacture that utilizes much existing manufacturing equipment. Once needle is retracted in the syringe of the invention, the syringe cannot be restored to functionality, as the hub flange is cut through and the stopper is cut through rendering the syringe substantially unusable and protecting the needle point from inadvertent contact by anyone. The syringe of the invention is capable of being retracted with a one-handed operation by the user and, once the needle is retracted, substantially functions as a self-contained "sharps" container.

BRIEF DESCRIPTION OF THE DRAWINGS

FIG. 4 is a cross-sectional view, analogous to FIG. 3a, showing the plunger partially proximal within the barrel;

FIG. 5 is a cross-sectional view, analogous to FIG. 3a, showing the plunger depressed distally beyond the distance necessary to expel liquids showing the flange cut;

FIG. 10 is a view of the hub, spring and sleeve assembly being positioned proximal to the distal portion of the barrel.

DETAILED DESCRIPTION

Figure 1:
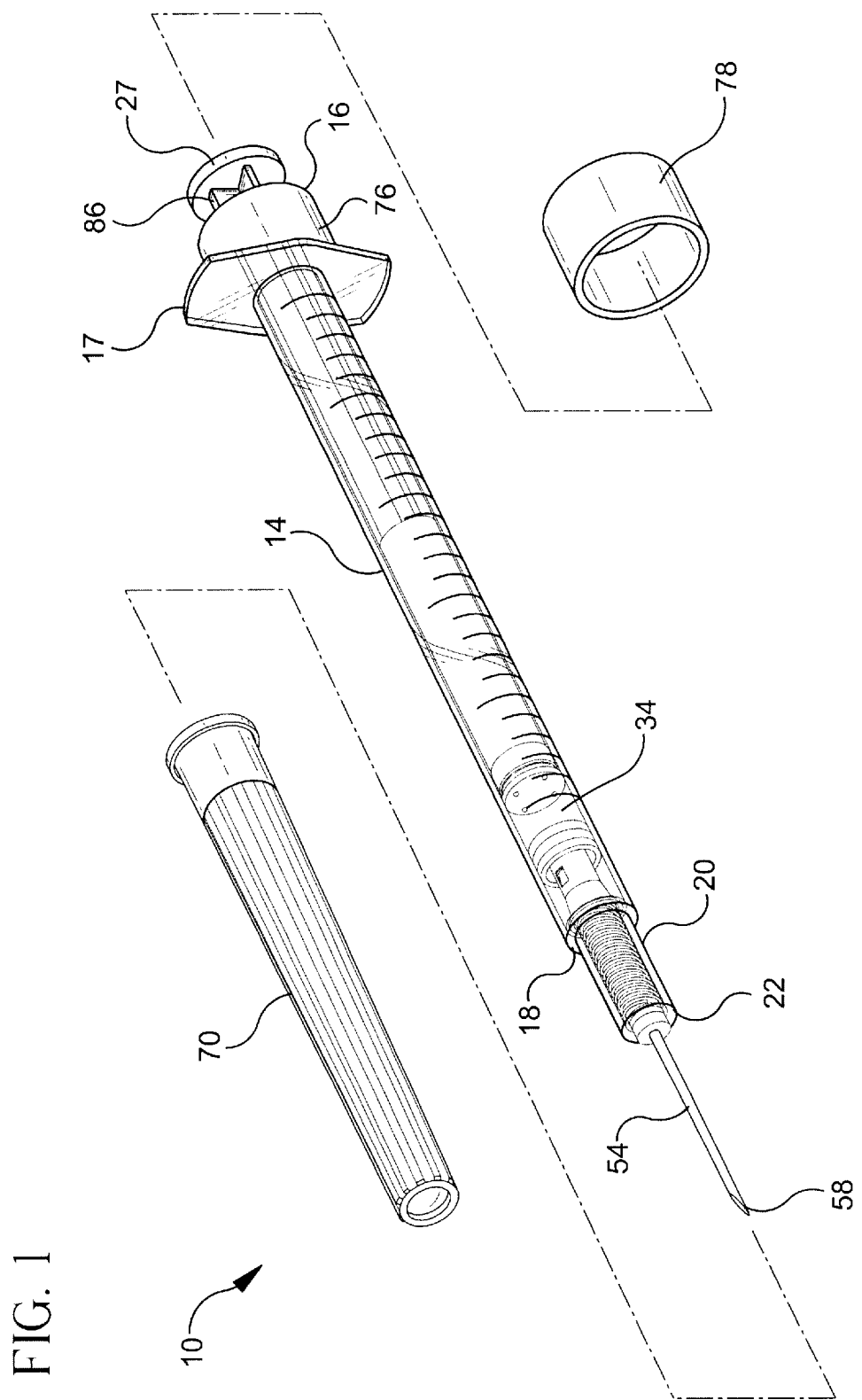
FIG. 1 is a partially exploded perspective view of a preferred embodiment of the syringe of the invention.

While this invention is satisfied by embodiments in many different forms, there are shown in the drawings and herein described in detail, embodiments of the invention with the understanding that the present disclosure to be considered as exemplary of the principles of the present invention and is not intended to limit the scope of the invention to the embodiments illustrated. The scope of the invention is measured by the appended claims and the equivalents. In this disclosure, a convention is followed wherein the distal end of the device is the end closest to a patient and the proximal end of the device is the end away from the patient and closest to a practitioner.

Referring to FIGS. 1–11, a hypodermic syringe 10 of the invention includes an elongate barrel 14 having an open proximal end 16 and an open distal end 18 defining a receiver 20 with an inward shoulder 22. Barrel 14 has a hollow bore 24 therethrough extending from proximal end 16 to distal end 18. Proximal end 16 preferably includes a finger grip 17 to assist a user in gripping and using the syringe. Syringe 10 includes an elongate plunger 26 with a proximal end 28 and a distal open end 30. Plunger 26 has a cavity 32 therewithin extending proximally from distal end 30. Plunger 26 is disposed and sized to fit within bore 24 of barrel 14 for a slidable movement to define a chamber 34 for receiving and expelling fluids. Plunger 26 has a stopper 36 disposed at distal end 30 to occlude the open end of cavity 32. Stopper 36 is sized and shaped to form a slidably substantially fluid tight seal with bore 24 of the barrel for forming chamber 34. Syringe 10 of the invention has an elongate hub 38 with a proximal flange 40. Hub 38 is disposed within and sized for slidable movement within receiver 20 at distal end 18 of the barrel with flange 40 defining a distal end of chamber 34 in the barrel. Hub 38 has a passageway 44 therethrough. There is a sleeve 46 sized to fit with a clearance about the hub, the sleeve being disposed about the hub between the shoulder 22 and flange 40 when hub 38 is disposed in receiver 20. Sleeve 46 has a sharpened proximal end to function as a cutting surface 48 disposed substantially against the distal surface of the flange 40, sleeve 46 having at least one inward projection 52 located distally to cutting surface 48. There is an elongate needle 54 with a fluid path therethrough. Needle 54 has a pointed distal end 58 and a proximal end 60 connected to passageway 44 of the hub so that when hub 38 is disposed in receiver 20 at the distal end of the barrel, pointed end 58 of the needle extends distally outwardly and fluid path of the needle is in fluid communication with chamber 34 of the barrel.

Figure 11:
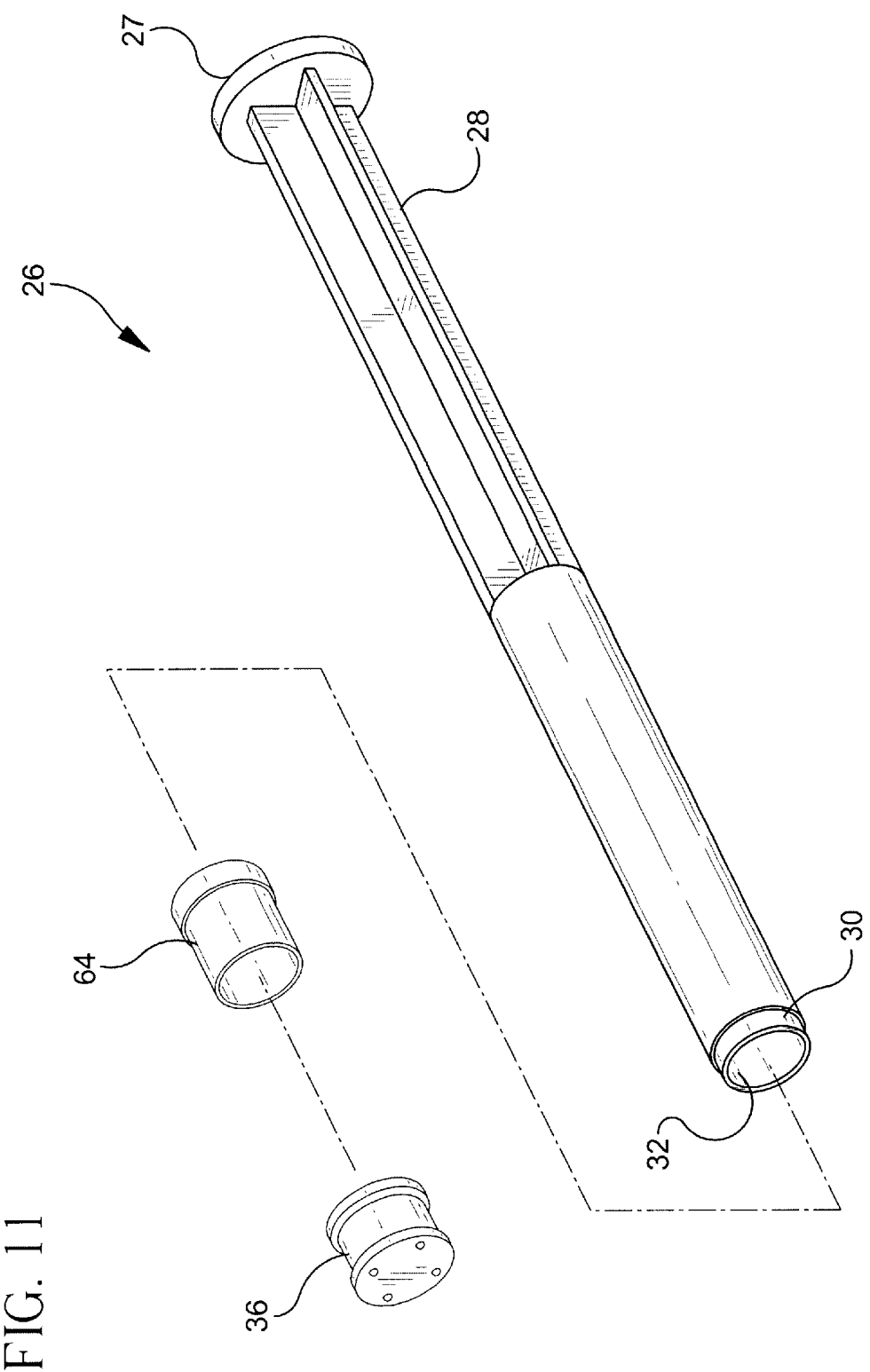
FIG. 11 is an exploded perspective view of the plunger of the invention.

Distal end 30 of plunger 26 preferably further includes an anvil 64, best seen in FIG. 11, and stopper 36 includes a proximal void 66. Anvil 64 is preferably disposed within void 66 in stopper 36 to engage cutting surface 48 of sleeve 46 when the cutting surface of the sleeve engages stopper 36, anvil 64 thereby facilitating the cut by cutting surface 48 by providing a shearing action with the cutting surface through stopper 36 to expose cavity 32 in plunger 26. Plunger 26 preferably includes a proximal finger press is 27 located at the proximal end 28 to facilitate movement of the plunger.

Figure 7:
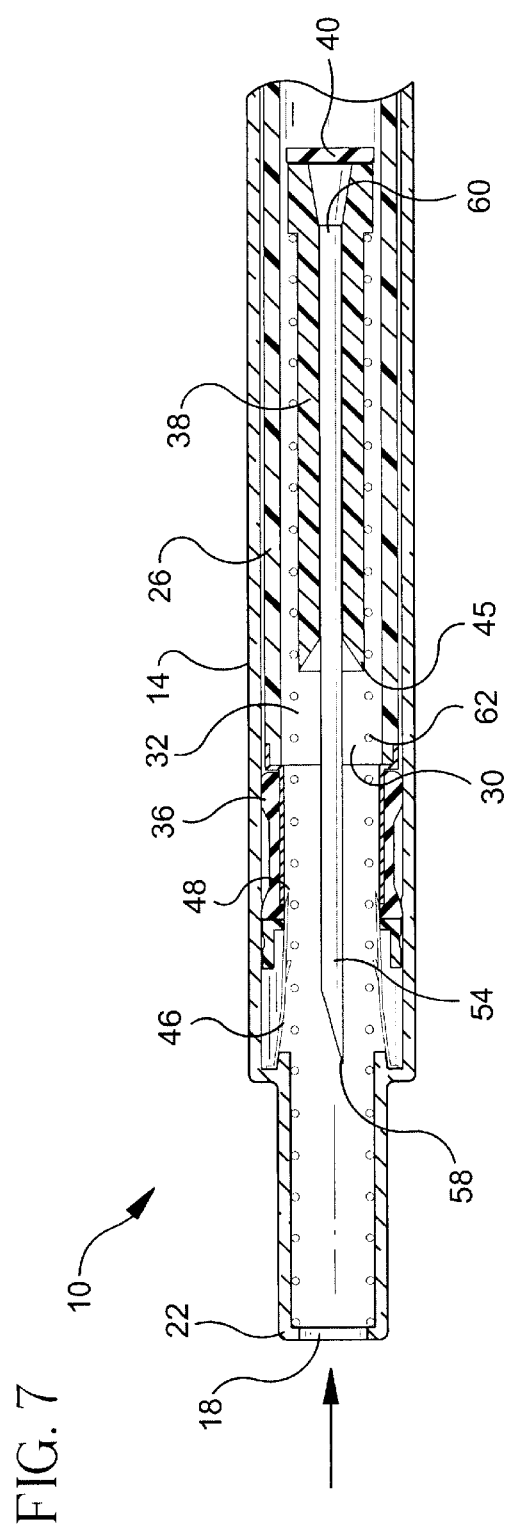
FIG. 7 is a cross-sectional view, analogous to FIG. 3a, showing the hub and needle withdrawn into the syringe.

Referring to FIGS. 3–7, a description of the use of syringe 10 to draw and expel fluid from chamber 34 and the selective withdrawal of needle 54 into syringe 10 so that distal point 58 of the needle is substantially protected from inadvertent exposure is shown. FIG. 4 illustrates the proximal movement of plunger 26 within barrel 14 to cause expansion of chamber 34 to draw fluid. FIG. 5 shows plunger 26 being moved distally to a position beyond that required to expel any fluid contained in chamber 34 causes cutting surface 48 to cut through flange 40. This distal movement also causes hub 34 to engage inward projection 52 on sleeve 46 to prevent distal movement of the hub, best seen in FIG. 6 and allow cutting surface 48 cut through stopper 36 to expose cavity 32 in plunger 26. The presence of preferred anvil 64 on the distal end of the plunger facilitates the cutting of plunger 36. As shown in FIG. 7, once stopper 36 is cut through, spring 62 urges hub 38 to move into cavity 32 a sufficient distance to withdraw needle 54 into syringe 10 so that inadvertent access to sharpened distal point 58 of the needle is substantially prevented.

Figure 9:
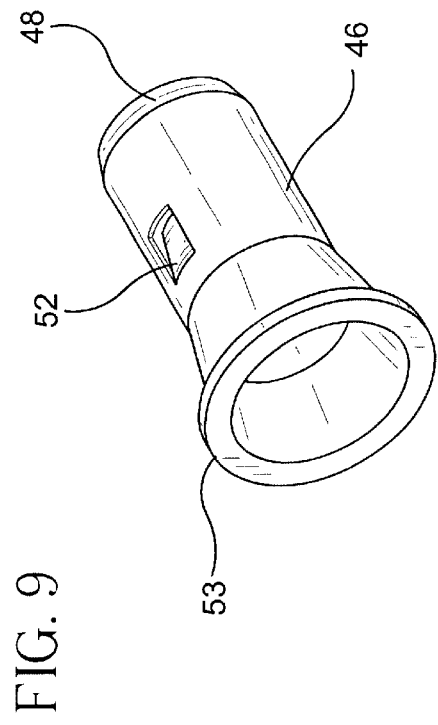
FIG. 9 is a perspective view of a preferred embodiment of the sleeve.
Figure 9A:
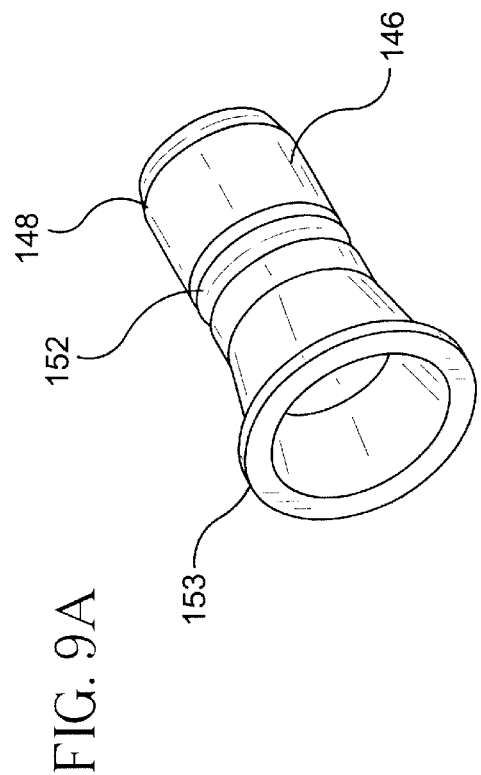
FIG. 9a is a perspective view of another embodiment of the sleeve.

Referring to FIGS. 9 and 9a, a preferred embodiment of sleeve 46 is shown in FIG. 9 and an alternate embodiment, sleeve 146 is shown in FIG. 9a. In the alternate embodiment, similar features having similar function are given similar reference characters with the addition of the "hundreds" digit. The sleeve is preferably formed from a metallic material, preferably stainless steel or the like, and formed into the desired shape by a deep drawing process. Following the forming, the sleeve is subjected to an electro-etching process that sharpens edge 48, 148 as well as cleaning and polishing the inside and the outside of the sleeve. Other methods of forming including, but not limited to, stamping, machining, powdered metal sintering and the like, are used for forming parts similar to sleeve 46 and operations such as grinding, honing and stropping are also useful for forming cutting surface 48 and are considered within the scope of the invention. Inward projection 52 either may be formed in the initial preferred deep draw process used for forming sleeve 46, or as a secondary operation. In the alternate embodiment illustrated in FIG. 9a, projection 152 is formed as one or more continuous inward ribs that serve to engage hub 38 during the cutting of stopper 36. Similar methods and materials are suitable for forming anvil 64.

Preferably sleeve 46 and 146 include a foot portion 53 and 153 respectively to support the sleeve at the distal end of barrel 14. Preferably, barrel 14 and receiver 20 form an interface 21 that serves to receive foot portion 53 or 153 when the sleeve is disposed in the barrel.

Figure 8:
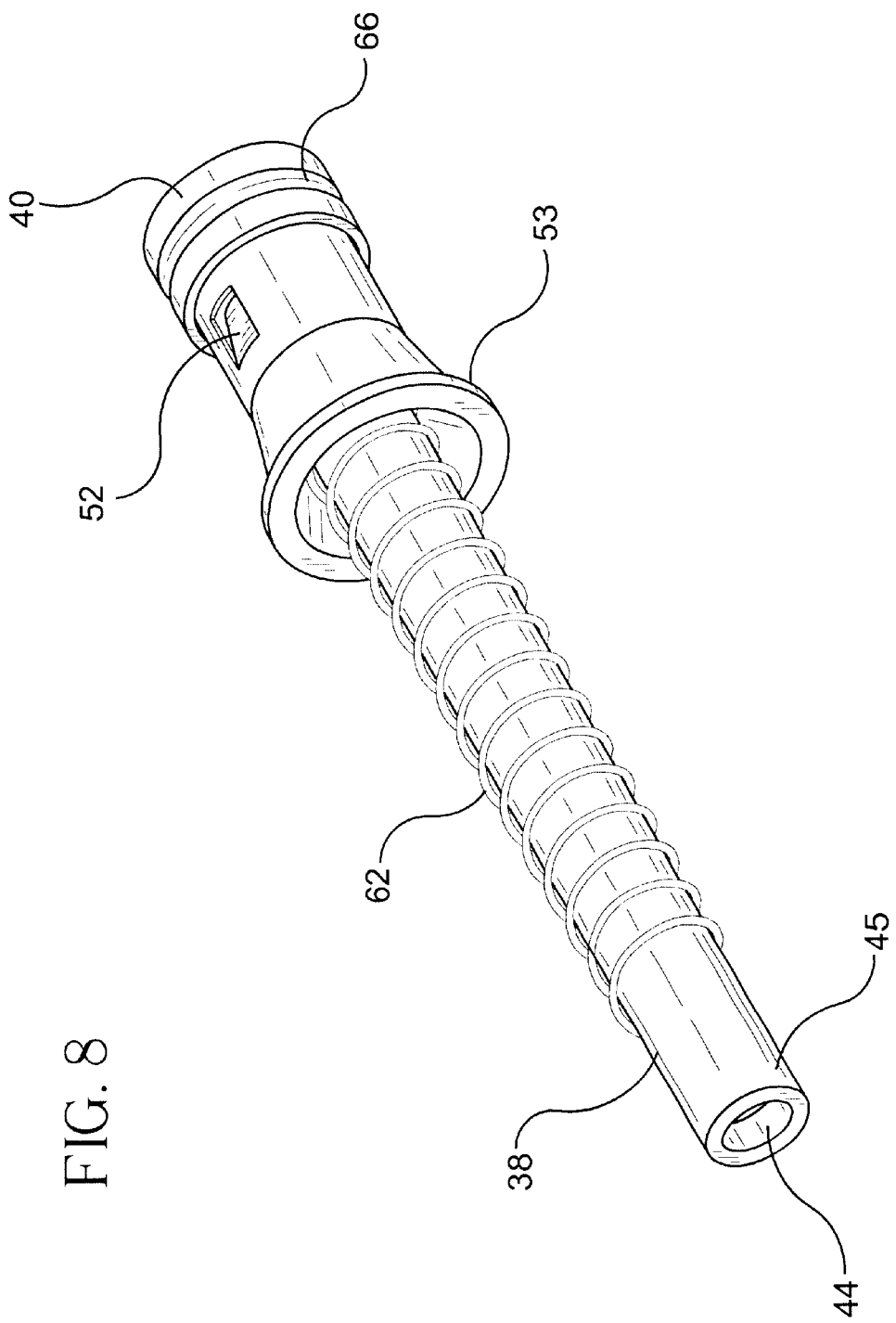
FIG. 8 is an enlarged view of the hub and flange with the spring and sleeve mounted thereon.

Referring now to FIG. 8, an assembly including hub 38, spring 62 and sleeve 46 is put together by placing spring 62 over hub 38 to engage flange 40 and then sleeve 46 is placed over the spring to engage the distal side of flange 40. This assembly is then introduced, see FIG. 10, into open proximal end 16 of barrel 14 and moved distally through bore 24 to a position where a depression 66 engages an inward projection 68 on the inside surface of bore 24. When flange 40 is positioned so that depression 66 engages inward projection 66, hub 38 is retained in barrel 14, spring 62 is in a compressed state between flange 40 and shoulder 22 and foot 53 is disposed at interface 21. A distal end 45 of hub 38 is then available to receive needle 54 using conventional cannulation apparatus. Preferably, as shown in the Figs., distal end 45 of the hub projects beyond shoulder 22 of the receiver. The needle cannulation process preferably includes application of a preselected amount of an adhesive adjacent to proximal end 60 of the needle and positioning the needle in passageway 44 of hub 38 so that sharpened end 58 projects distally outwardly and fluid path of the needle is in fluid communication with chamber 34 of the barrel. The adhesive serves to bond needle 54 into hub 38. Once needle 58 is positioned and bonded into hub 38, a lubricant may be applied to the needle using the same equipment used for conventional non-retractable fixed needle syringes. At this time, a shield 70 is placed over needle 54 to engage receiver 20. Shield 70 serves to protect sharpened point 58 from inadvertent exposure or damage during handling prior to its intended use.

Figure 2:
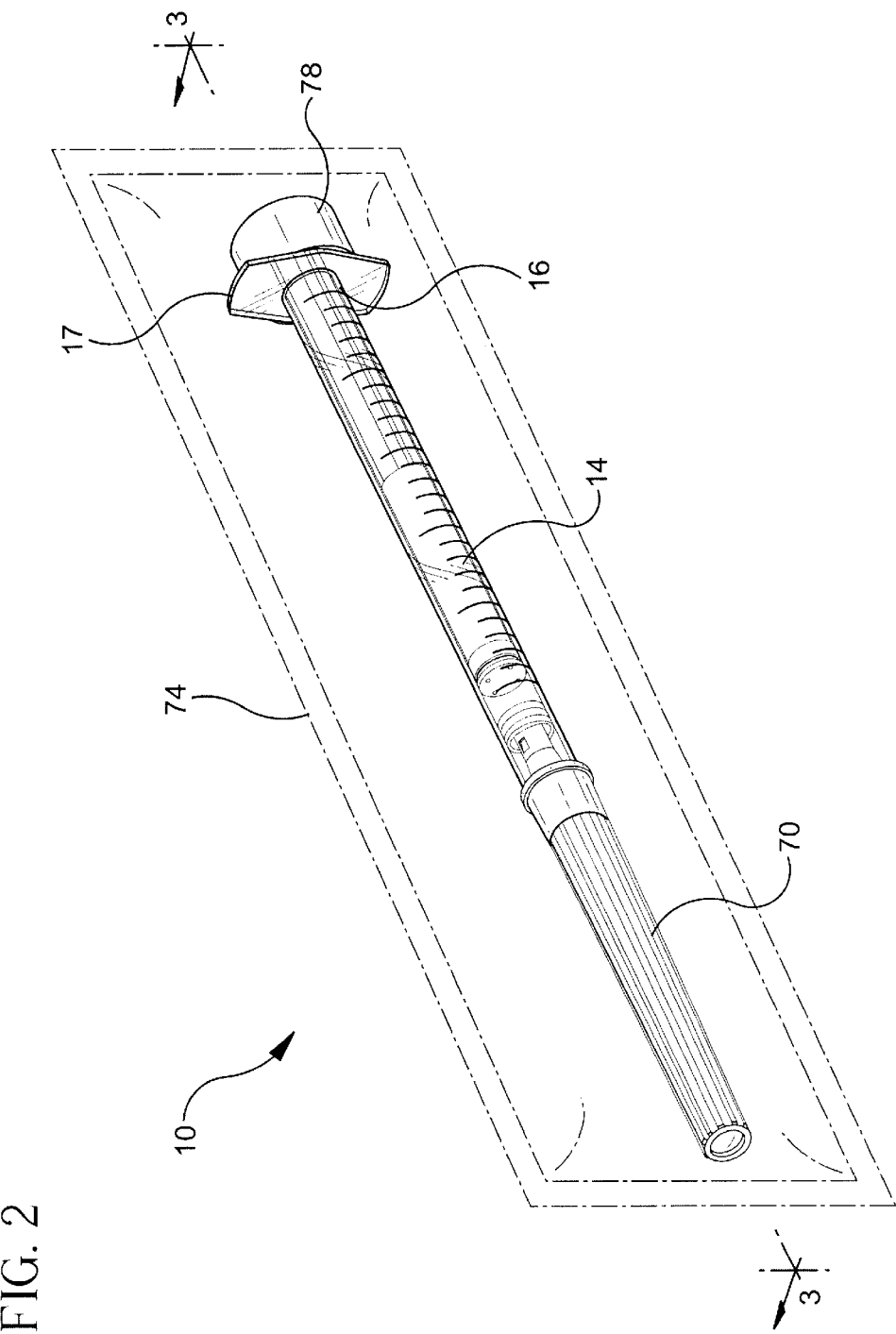
FIG. 2 is a perspective view of the syringe of FIG. 1 in a package.
Figure 3:
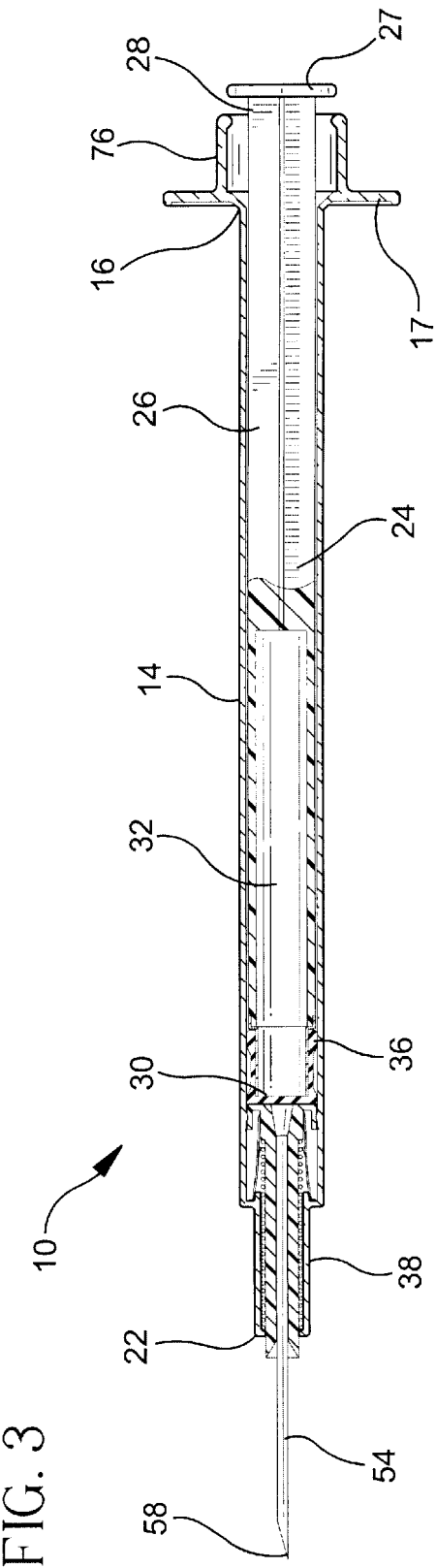
FIG. 3 is a cross-sectional view of the invention of FIG. 2 taken along the line 3—3.
Figure 3A:
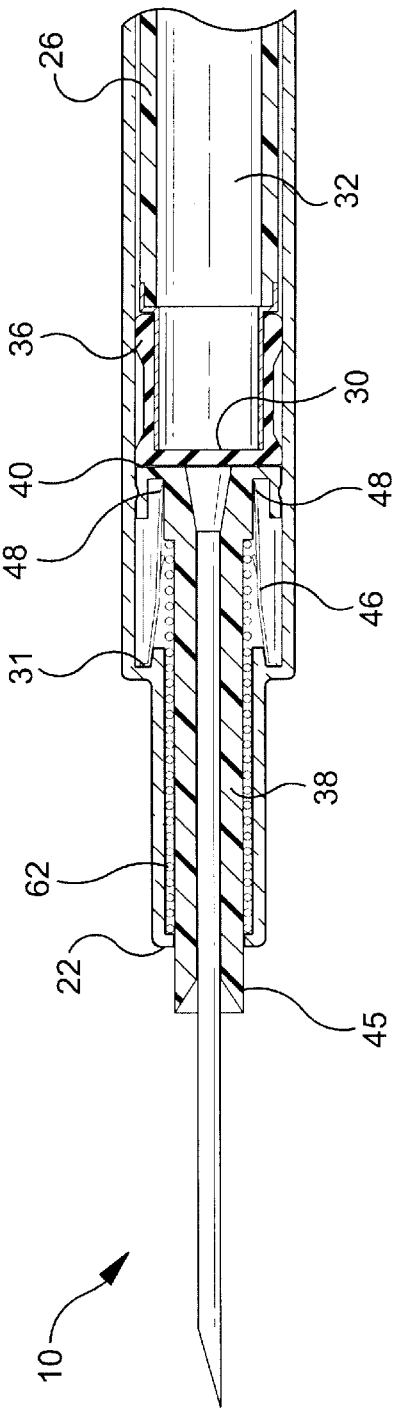
FIG. 3a is a partial cross-sectional view of the invention, taken from FIG. 3.
Figure 6:
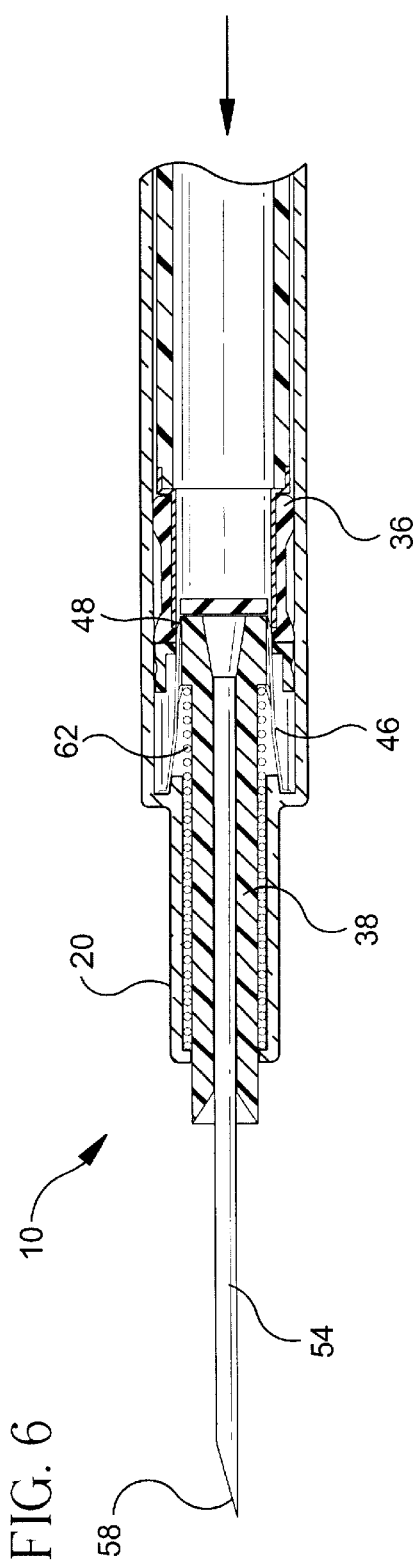
FIG. 6 is a cross-sectional view, analogous to FIG. 3a, showing the plunger cut.

For some applications, it may be preferred to place syringe 10 with shield 70 in a package 74, best seen in FIG. 2, formed from materials substantially resistant to the passage of microorganisms as a final package. Alternatively, barrel 14 may include a collar 76 at proximal end 16 of the barrel. As illustrated in FIG. 1, a cap 78 may be placed on collar 76 to cover plunger 26 and occlude open proximal end 16 that, in conjunction with shield 70, to render syringe 10 "self-contained". A self-contained syringe is considered to be self packaged in that all components of the syringe that are considered "fluid-path" are substantially protected from outside contamination as long as cap 78 and shield 70 are intact. Cap 78 and shield 70 preferably include tortuous path venting to the atmosphere. The venting allows positioning and exercise of plunger 26 during assembly without displacement of shield 70. Preferably, either after assembly of syringe 10 with cap 78 and shield 70 or placement of syringe 10 in package 74 with just shield 70, the syringe is exposed to conditions that substantially render any microorganism inside the package or within the fluid path of the syringe non-viable. Suitable conditions for rendering microorganisms non-viable include, but are not limited to exposure to ionizing radiation such as gamma, electron-beam and ultraviolet; chemical agents such as ethylene oxide, vapor phase hydrogen peroxide and the like. After sufficient exposure, syringe 10 is considered sterile until package 74 is opened or until shield 70 and cap 78 are removed.

Preferably, package 74 is constructed so that it provides tamper evidence of its being opened. Preferably, cap 78 and shield 70 are affixed to syringe 10 with a frangible label, heat-stake or the like that provide the user with tamper evidence of any removal or disruption of the cap and shield. When materials are selected for forming the components of syringe 10 and package 74, consideration should be given to the intended sterilization method to ensure that the materials selected are compatible with the sterilization method.

Suitable materials for forming barrel 14 include, but are not limited to, thermoplastic materials such as polypropylene, polyethylene, polycarbonate and the like. Polypropylene is preferred. Suitable materials for forming plunger 26 include thermoplastics such as filled polystyrene, polypropylene and the like. Filled polystyrene is preferred. Hub 38 may be formed from thermoplastic materials such as polypropylene, polystyrene, polyethylene and the like, with polypropylene being preferred. Cap 78 may be formed from thermoplastic materials such as polyethylene, polyproplyene, polycarbonate and the like, with polyethylene being preferred. Shield 70 may be formed from thermoplastic materials such as polyethylene, polypropylene and the like, with polyethylene being preferred.

Stopper 36 may be formed from a thermoplastic material such as styrene block copolymer and the like. Alternatively, a thermoset material such as natural rubber or synthetic rubber may be used. Preferably, the material selected is somewhat resilient so that stopper 36 readily forms a fluid tight seal with the inside surface of bore 24 of the barrel.

Spring 62 is preferably formed from a metallic material such as a stainless steel wire. By forming spring 62 from stainless steel wire, the gauge of the wire and the number of turns of the spring can be selected to provide spring 62 with sufficient bias when it is compressed between shoulder 22 and flange 40 to urge hub 38 into cavity 32 once flange 40 and stopper 36 are cut to expose the cavity.

Syringe 10 of the invention offers several real benefits to the art of drug delivery. Syringe 10 has similar function and utility to conventional non-retractable syringes. Unlike many of the syringes previously disclosed, syringe 10 of the invention has little "dead-space", i.e., undeliverable volume contained in chamber 34 that would confound measurement of mixing insulins in the syringe, a common practice. Syringe 10 offers selective and reliable retraction of needle 54 to a position within the syringe that substantially prevents inadvertent exposure to sharpened point 58 of the needle. The components used to provide the selective needle retraction capability are substantially compatible with the equipment used in the manufacture of conventional non-retractable syringes. The components used to provide the retraction capability are readily produced in a small enough size to fit within the bore of a one cc syringe with a diameter of about one quarter inch. Additionally, the components used to provide the retraction capability are relatively simple and straightforward to assemble. Many of the previously disclosed retractable needle syringes are complex, difficult to manufacture and assemble. Additionally, the activation of these previously disclosed retraction mechanisms either is not compatible with much common usage of the syringes, i.e. mixing of insulins, or is dependent on balancing the forces required to expel the syringe contents against the force required to activate the retraction mechanism. Syringe 10 of the invention provides users of small capacity syringes with the benefit of selective retractability of the needle and provides the capability for efficient manufacture of the large numbers of syringes required by the market by being relatively simple to manufacture and assemble as well as the ability to utilize much of the equipment used to produce conventional syringes.

What is claimed is:

1. A hypodermic syringe with a selectively retractable needle comprising:

an elongate barrel having an open proximal end and a distal end defining a receiver with an inward shoulder, said barrel having a hollow bore therethrough extending from said proximal end to said distal end;

an elongate plunger having a proximal end and an open distal end, said plunger having a cavity therewithin extending proximally from said distal end, said plunger being disposed and sized to fit within said bore of said barrel for a slidable movement to define a chamber for receiving and expelling fluids, said plunger having a stopper disposed at said distal end to occlude said open end of said cavity, said stopper being sized and shaped to form a slidably substantially fluid tight seal with said bore of said barrel for forming said chamber;

an elongate hub having a proximal flange, said hub disposed within and sized for slidable movement within said receiver at said distal end of said barrel with said flange defining a distal end of said chamber in said barrel, said hub having a passageway therethrough;

a sleeve sized to fit with a clearance about said hub, said sleeve being disposed about said hub between said shoulder and said flange, said sleeve having a sharpened proximal end disposed substantially against a distal surface of said flange, said sleeve having at least one inward projection located distally to said cutting surface;

an elongate needle having a fluid path therethrough, said needle having a pointed distal end and a proximal end connected to said passageway of said hub so that when said hub is disposed in said receiver in at said distal end of said barrel, said pointed end of said needle extends distally outwardly and said fluid path of said needle is in fluid communication with said chamber of said barrel;

an elongate spring disposed about said hub sufficiently compressed to provide a bias between said receiver and said flange so that when a force greater than a force required to expel fluid from said chamber is applied to said plunger, said hub is moved distally in said receiver against said bias of said spring a sufficient distance to cause said cutting surface of said sleeve to engage and to cut through said flange and to engage said at least one inward projection on said sleeve against said hub to allow said cutting surface of said sleeve to cut through said stopper to expose said cavity in said plunger thereby to allow said bias of said spring to urge a sufficient movement of said hub into said cavity in said plunger to retract said needle to a position within said syringe where inadvertent contact with said pointed distal end is substantially prevented.

2. The retractable needle syringe of claim 1 wherein said distal end of said plunger further includes an anvil and said stopper includes a proximal void, said anvil being disposed within said void in said stopper to engage said cutting surface of said sleeve when said cutting surface of said sleeve engages said stopper, said anvil thereby facilitating the cut by said cutting surface through said stopper to expose said cavity in said plunger.

3. The retractable needle syringe of claim 2 wherein said anvil is formed from a metallic material.

4. The retractable needle syringe of claim 1 wherein said receiver is sized so that said open distal end of said barrel defining said receiver is sized and shaped to allow a slidable movement of said hub while retaining said spring about said hub.

5. The retractable needle syringe of claim 1 wherein said sleeve is formed into a tapered shape wherein said proximal end of said sleeve has a smaller diameter than a distal end of said sleeve, thereby facilitating a stretching of said stopper when said resilient stopper is cut by said cutting surface.

6. The retractable needle syringe of claim 5 wherein said sleeve is formed from a metallic material.

7. The retractable needle syringe of claim 6 wherein said sleeve is subjected to an electrochemical treatment thereby enhancing said cutting surface's sharpness properties.

8. The retractable needle syringe of claim 6 wherein said metallic material is stainless steel.

9. The retractable needle syringe of claim 1 wherein said proximal end of said barrel further comprises a finger flange for assisting a practitioner's grip of said syringe during a use.

10. The retractable needle syringe of claim 9 wherein said finger flange further includes a collar projecting proximally a sufficient distance, said collar being disposed and shaped to receive a removable cap for covering said plunger and wherein said receiver at said distal end of said barrel is shaped to receive a removable shield for protecting said sharp distal end of said needle.

11. The retractable needle syringe of claim 10 wherein said cap disposed on said collar and said shield disposed on said receiver is sufficiently to substantially prevent passage of any microorganisms beyond said cap and said shield, and wherein said syringe is exposed to conditions that substantially render any microorganisms therein non-viable.

12. The retractable needle syringe of claim 11 wherein said cap and said shield are each provided with a frangible attachment, whereby neither said cap nor said shield are removable from said collar and said receiver respectively without disruption of said attachments, thereby providing a positive evidence to the practitioner that once said cap and said shield are positioned on said collar and said receiver, they have not been removed prior to the intended use, thereby providing a "tamper-evidence".

13. The retractable needle syringe of claim 1 wherein said spring is formed from a metallic material.

14. The retractable needle syringe of claim 1 being placed in a package formed from materials substantially resistant to the passage of microorganisms and exposed to conditions that render any microorganisms therein substantially non-viable.

15. The retractable needle syringe of claim 1 wherein said bore of said barrel further comprises an inward projection and said flange on said hub includes a cooperating recess so that when said hub is positioned in said receiver, said depression in said flange engages said projection in said barrel thereby retaining said hub.

16. A method for assembling a retractable needle syringe comprises:

providing an elongate barrel having an open proximal end and an open distal end defining a receiver with an inward shoulder, said barrel having a hollow bore therethrough extending from said proximal end to said distal end;

providing an elongate hub having with a proximal flange and a distal tip, said hub disposed within and sized for slidable movement within said receiver at said distal end of said barrel with said flange defining a distal end of said chamber in said barrel, said hub having a passageway therethrough;

placing an elongate spring about said hub;

placing a sleeve sized having a sharpened proximal end and sized to fit with a clearance about said hub over said spring with said sharpened proximal end being located distally to said flange and said hub thereby forming an assembly;

inserting said assembly into said barrel from said proximal end of said barrel to a position wherein at least a portion of said distal tip of said hub projects distally from said receiver, so that said spring is compressed between said flange and said shoulder;

providing an elongate needle having a fluid path therethrough, said needle having a pointed distal end and a proximal end;

mounting said needle into said distal tip of said receiver so that said fluid path of said needle is connected to said passageway of said hub with said pointed end of said needle extending distally outwardly and said fluid path of said needle is in fluid communication with said chamber of said barrel;

providing an elongate plunger with a proximal end and a distal open end, said plunger having a cavity therewithin extending proximally from said distal end, said plunger being sized to fit within said bore of said barrel for a slidable movement to define a chamber for receiving and expelling fluids, said plunger having a stopper disposed at said distal end to occlude said open end of said cavity, said stopper being sized and shaped to form a slidably substantially fluid tight seal with said bore of said barrel for forming said chamber; and placing said distal end of said plunger into said proximal end of said barrel thereby assembling said syringe having said retractable needle.

* * * * *